(12) United States Patent
Bakker et al.

(10) Patent No.: US 7,557,916 B2
(45) Date of Patent: Jul. 7, 2009

(54) SPECTROSCOPIC SYSTEM WITH MULTIPLE PROBES

(75) Inventors: Bernardus Leonardus Gerardus Bakker, Nijmegen (NL); Michael Cornelis Van Beek, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 158 days.

(21) Appl. No.: 11/570,137

(22) PCT Filed: Jun. 22, 2005

(86) PCT No.: PCT/IB2005/052045

§ 371 (c)(1),
(2), (4) Date: Dec. 7, 2006

(87) PCT Pub. No.: WO2006/003551

PCT Pub. Date: Jan. 12, 2006

(65) Prior Publication Data

US 2008/0062401 A1     Mar. 13, 2008

(30) Foreign Application Priority Data

Jul. 2, 2004    (EP) .................................. 04103151

(51) Int. Cl.
*G01J 3/30*    (2006.01)
(52) U.S. Cl. ..................................... 356/317
(58) Field of Classification Search .................. 356/301, 356/317–318, 417
See application file for complete search history.

(56) References Cited

U.S. PATENT DOCUMENTS

| 5,455,673 A | * | 10/1995 | Alsmeyer et al. | ............ 356/301 |
| 6,313,423 B1 | * | 11/2001 | Sommer et al. | ............. 356/301 |
| 2003/0142302 A1 | | 7/2003 | Jiang | |
| 2003/0142309 A1 | * | 7/2003 | Kuebler et al. | ............... 356/338 |
| 2005/0162646 A1 | * | 7/2005 | Tedesco et al. | ............... 356/301 |

FOREIGN PATENT DOCUMENTS

| EP | 1 052 499 A1 | 11/2000 |
| WO | 9819800 A1 | 5/1998 |
| WO | 02057758 A1 | 7/2002 |
| WO | 02057759 A1 | 7/2002 |

OTHER PUBLICATIONS

Angel, S.M., et al.; Simultaneous Multi-point Fiber-optic Raman Sampling for Chemical Process Control Using Diode Lasers and a CCD Detector; 1991; SPIE Chemical, Biochemical and Environmental Fiber Sensors; vol. 1587; pp. 219-231.

* cited by examiner

*Primary Examiner*—Kara E Geisel (57) ABSTRACT

The present invention provides a spectroscopic system for non invasive spectral analysis of substances or biological structures (114, 116) that are located in a plurality of various volumes of interest (110, 112). The inventive spectroscopic system makes use of a multiplicity of various probe heads (106, 108) that are connected to a base station (100) providing a spectroscopic light source (104) and spectroscopic analysis means (102). By additionally implementing a coupling unit (132) the present invention allows to realize a spectroscopic analysis environment that makes spectroscopic analysis available in a variety of different locations, e.g. various rooms of a hospital.

15 Claims, 9 Drawing Sheets

SPECTROSCOPIC SYSTEM WITH MULTIPLE PROBES

The present invention relates to the field of spectroscopic systems for analyzing properties of biological structures.

Usage of optical spectroscopy techniques for analytical purposes is as such known from the prior art. For example, WO 02/057758 A1 and WO 02/057759 A1 disclose spectroscopic analysis apparatuses for in vivo non-invasive spectroscopic analysis of the composition of a fluid flowing through a capillary vessel of a person. A light beam, preferably in the near infrared (NIR) range, is focused in a capillary vessel underneath the surface of the skin of the person. The interaction between the near infrared radiation and a substance located inside the capillary vessel is mainly governed by elastic and inelastic scattering processes. Typically, inelastic scattered radiation that is due to an inelastic scattering process, like a Raman scattering, is subject to a frequency shift that can be measured by means of spectral analysis. Hence the spectrum of scattered radiation is therefore indicative of various properties of a substance, e.g. blood that is located in a capillary vessel of a person. By spectral analysis of the inelastic scattered radiation the molecular composition of the substance can be precisely determined.

In order to obtain a sufficient signal to noise ratio for the spectroscopic signals it is important that an exciting light beam is exactly focused into a dedicated volume of interest. Therefore, spectroscopic systems are typically equipped with some kind of imaging system that allows to optically inspect an area of interest for selecting and tracking a dedicated biological structure into which the excitation beam has to be focused. Consequently, a spectroscopic system comprises at least three major components: an imaging system, a light source for generating excitation radiation, preferably in the NIR range, and a spectroscopic analysis device. In particular, the light source as well as the spectroscopic device have to meet stringent requirements in order to provide reliable and precise measurement results. Suitable devices that are nowadays available are rather expensive and appreciably render the cost of purchase of such a spectroscopic system to a high range.

It is also known in the prior art to divide the functionality of a spectroscopic analysis system into two components such as a base station and a flexible probe head. Preferably, the probe head is designed as a small, compact and flexible device for directing excitation radiation into the volume of interest and for collecting respective return radiation that provides the spectroscopic data. The probe head is connected to a base station providing a light source and the spectroscopic analysis unit. The probe head and the base station are connected by fiber optical transmission means that provide bidirectional transmission of optical signals between the probe head and the base station. Since the rather spacious spectroscopic analysis unit and the light source are provided by the base station, the probe head can be designed in a compact and flexible way. This allows a flexible handling in order to access arbitrary regions of a body that are usually difficult to examine.

The present invention aims to provide a spectroscopic system making more efficient use of a light source and a spectroscopic analysis unit.

The present invention provides a spectroscopic system for determining of a property of a substance in at least first and second volumes of interest. The spectroscopic system comprises a base station and at least a first and a second probe head. The base station has a light source and a spectroscopic analysis unit. Preferably, the light source is implemented as a near infrared laser and the spectroscopic analysis unit is based on a dispersive element such as a grating and a highly sensitive noise reducing cooled CCD camera. The at least first and second probe heads are adapted to be coupled to the base station for directing at least a first and a second excitation radiation into the at least first and second volumes of interest and for collecting at least a respective first and second return radiation.

The invention therefore provides effective means to share the functionality of the relative expensive components of a spectroscopic analysis system, the laser light source and the spectroscopic analysis unit, among a plurality of probe heads. Hence, the invention provides a universal and modular concept for making most effective usage of the rather costly components of a spectroscopic analysis system.

Each one of the at least first and second probe heads is adapted to focus excitation radiation into a respective volume of interest and to collect appropriate return radiation for spectroscopic analysis. The multiple probe heads are by no means correlated to each other. They can be utilized individually and allow for a universal application of a spectroscopic analysis. Typically, the probe heads are connected to the base station by means of flexible fiber optic components. For example, various probe heads can be attached to different parts of a body of a person thereby allowing efficient spectroscopic inspection of substances that are located in different regions of the respective body.

The inventive spectroscopic system is by no means restricted to in vivo analysis of substances in a human body, like e.g. blood. Moreover, it is universally applicable to various analysis and measurement scenarios including for example in vitro analysis of blood samples.

Additionally, application of various probe heads is by no means restricted to a single person. Various scenarios are conceivable where different probe heads can be used for spectroscopic analysis that has to be applied to different persons that are even located in different rooms. Additionally, the probe heads can be operated in an entirely individual way. They can be used to determine different properties of different substances in various volumes of interest. Also, depending on the dedicated application, intensity as well as the frequency of the at least first and second excitation radiation may be individually modified. Even though the inventive spectroscopic system is dedicated to applications in the framework of medical diagnostics it could also be applied to any other spectroscopic analysis system allowing for a modular assembly of a base station and a plurality of probe heads.

Furthermore, according to the invention, a volume of interest may not only specify a volume of a body of a person or an animal. Generally, a volume of interest refers to any kind of material, substance or matter that is suitable for respective spectroscopic analysis. Thus, the inventive spectroscopic system is by no means limited to applications of spectroscopic analysis within the framework of biological structures and biological formations. For example, the inventive spectroscopic system may be applied for in vitro analysis of blood samples as well as for detection and analysis of explosives or drugs.

According to a further preferred embodiment of the invention, the spectroscopic system further comprises an imaging unit that is adapted to provide at least a first image of a first area of interest and a second image of a second area of interest. The imaging unit effectively allows to obtain a visual image of an area of interest prior to application of relatively high excitation radiation to a corresponding volume of interest. Visual inspection of an area of interest effectively allows to allocate and to track for example particular biological structures like blood vessels that are of particular interest for the spectroscopic analysis. Making use of an imaging unit in combination with some kind of alignment or positioning means allows to retrieve a particular biological structure and to effectively focus excitation radiation into the biological structure by making use of optical alignment means and/or various positioning means.

The imaging system can in principle based on various different techniques, such as Orthogonal Polarized Spectral Imaging (OPSI), Confocal Video Microscopy (CVM), Optical Coherence Tomography (OCT), Confocal Laser Scanning, Microscopy (CLSM), Doppler based imaging and ultrasound based imaging and laser speckle imaging. The imaging unit can in principle be implemented in a plurality of different ways. The imaging unit can for example be implemented as a component of the base station, as a separate device or it can be incorporated into each one of the at least first and second probe heads.

Preferably, a probe head serves as a universal optical component for both the spectroscopic analysis unit and the imaging unit. Typically, the probe head comprises an objective lens that is adapted for focusing of excitation radiation, for collecting of return radiation and for gathering visual information of an area of interest that is to be processed by the imaging unit. Separation of the various optical signals, spectroscopic and imaging signals can effectively be realized by making use of different wavelengths for spectroscopic analysis and imaging and by implementing a dichroic mirror element that features wavelength selective transmission and reflection properties.

According to a further preferred embodiment of the invention, the spectroscopic system further comprises a coupling unit that provides a coupling between the base station and any of the at least first and second probe heads. The coupling unit serves as a kind of optical multiplexer, router or switch. Preferably, the multiplexer is connected to all of the at least first and second probe heads by some kind of fiber optical transmission medium and is further connected to the base station by making use of at least one optical transmission medium.

Usage of the coupling unit provides a whole diversity of different application scenarios and a large variety of possible implementations. It makes spectroscopic analysis universally available to different locations and allows to analyze different regions of a body or different persons simultaneously. For example, the inventive spectroscopic system can be implemented in a hospital by installing the base station in a dedicated examination room and providing all other rooms with a coupling device that is connected to the base station. Implementing the flexible probe heads and their corresponding fiber optic transmission media as pluggable devices, spectroscopic analysis can be effectively performed in almost every room of a hospital by plugging the probe heads into an appropriate coupling unit. Hence the coupling unit enables the implementation of a fiber optical network that is specifically adapted for transmission of spectroscopic and imaging optical signals.

According to a further preferred embodiment of the invention, the coupling unit is adapted to split a radiation generated by the light source of the base station into the at least first and second excitation radiation. Moreover, the coupling unit is further adapted to couple the at least first and second excitation radiation to the at least first and second probe heads. In this way, the coupling unit provides an effective splitting of the radiation generated by the near infrared laser of the base station into a plurality of light beams that are coupled to the various probe heads. Consequently, for transmission of light from the base station to the coupling device only a single optical fiber is needed.

Splitting of received radiation can be realized by means of e.g. beam splitters, dedicated filters or other refractive or diffractive optical components. Depending on the specific application of the various probe heads the radiation received from the light source of the base station can be split into components of equal or different intensity. These components are then coupled into the various optical fiber transmission media that provide optical transmission to the various probe heads that are connected to the coupling unit.

According to a further preferred embodiment of the invention, the coupling unit is further adapted to couple the at least first and second return radiations collected by the at least first and second probe heads into at least a first and a second fiber transmission medium that are connected to the base station. In this embodiment the at least first and second fiber transmission media provide unidirectional transmission of return radiation from the coupling unit to the base station, in particular to the spectroscopic analysis unit of the base station. Hence transmission of excitation radiation from the base station to the coupling unit can be realized by a single optical fiber but transmission of collected return radiation of the various probe heads has to be transmitted separately either to the coupling unit or alternatively directly to the base station.

According to a further preferred embodiment of the invention, the spectroscopic system comprises a control module that is adapted to control the coupling of the at least first and second excitation radiation to the at least first and second probe heads and to control the coupling of the at least first and second return radiation to the base station. Hence, the control module controls an interplay between the base station, the coupling unit and the various probe heads. By means of the control module a user of the spectroscopic system may select and activate a particular probe head or spectroscopic analysis of the substance being located in a respective volume of interest. By means of the control module, required excitation radiation is coupled into the selected probe head and corresponding return radiation is conducted into the spectroscopic analysis unit of the base station.

Moreover, the control module is also adapted to control the imaging unit. In particular when the imaging unit is implemented in the base station or as a separate device, the control module appropriately configures all components of the spectroscopic system that are necessary for providing an image of a first area of interest by means of a display of the imaging unit, focusing a first excitation radiation into the first volume of interest by making use of the first probe head, collecting first return radiation and conducting the collected return radiation to the spectroscopic analysis unit. Hence, the control module provides a correct mapping between collected spectroscopic data and imaging signals.

In another aspect, the invention provides a coupling unit of a spectroscopic system for determining of a property of a substance in at least first and second volumes of interest. The spectroscopic system has a base station and has at least a first and a second probe head. The inventive coupling unit comprises coupling means for providing a coupling between the base station and the at least first and second probe heads of the spectroscopic system. The coupling unit comprises as least a first optical coupling element that is adapted for optical coupling to the base station and further comprises at least a second and a third coupling element that are adapted for optical coupling to the at least first and second probe heads.

The coupling means of the coupling unit are adapted to couple excitation radiation received from the base station to any one or two several of the at least first and second probe heads. The optical coupling elements thereby provide effective means for coupling of radiation or an optical beam into a fiber transmission medium. Hence the first coupling element provides efficient coupling of radiation generated by the light source of the base station into the coupling unit and the second and the third coupling elements are adapted for coupling of light into optical fibers that are connected to the at least first and second probe heads. Preferably, the optical coupling elements are implemented as pluggable elements that allow an easy and effective reconfigurable plugging of different probe heads to the coupling unit.

According to a further preferred embodiment of the invention, the coupling means are further adapted to couple a radiation received from the base station as first excitation radiation into the first of the at least first and second probe heads and being further adapted to couple first return radiation collected by the first probe head into the base station. Here, coupling refers to coupling of radiation into respective fiber optical transmission media that provide transmission of optical signals to and from the first probe head and the base station. In this embodiment the coupling unit serves as a router and is adapted for bidirectional transmission of optical signals between the base station and a particular probe head.

In another aspect the invention provides a base station of a spectroscopic system for determining of a property of a substance in at least first and second volumes of interest. The base station comprises a light source and a spectroscopic analysis unit and means for coupling the base station to at least a first and a second probe head. The at least first and second probe heads are adapted to direct a first and a second excitation radiation into the first and second volumes of interest and to collect at least a respective first and second return radiation.

According to a further preferred embodiment of the invention, the spectroscopic analysis unit of the base station is further adapted to spectrally analyze the at least first and second return radiation simultaneously. The first and second return radiation are collected from the first and second volumes of interest that may be located in different parts of a body of a person. Alternatively, the at least first and second volumes of interest may belong to different persons that are located in different rooms of e.g. a hospital. Consequently, simultaneous analysis of various spectroscopic signals provides simultaneous and independent spectroscopic inspection of various biological structures that might even be at remote locations. In this sense simultaneous analysis also refers to an analysis that is performed within overlapping time intervals. In this way the first volume of interest of a first person can be spectrally analyzed irrespective of an ongoing spectral analysis of a substance in a second volume of interest of a second person. Hence, the spectral analysis can be performed in a plurality of different ways, either in simultaneous or subsequent mode or within partially overlapping time intervals. This allows for a large flexibility of the system and provides a vast range of different application scenarios.

In still another aspect the invention provides a computer program product for a spectroscopic system for determining of a property of a substance in at least first and second volumes of interest. The spectroscopic system has a base station and has at least a first and a second probe head. The computer program product comprises program means for selecting at least the first probe head of the at least first and second probe heads, program means for directing excitation radiation to the at least first and second probe head and program means for analyzing respective return radiation that is collected by the at least first probe head.

Preferably, the computer program product is executed by the control module of the base station. Alternatively, the control module can be implemented by a personal computer or a similar computing device that is adapted to control an interplay between the base station and in particular the spectroscopic analysis unit of the base station, the coupling unit and the probe heads.

Moreover, the computer program product is adapted to control functionality of the imaging unit. In this way the computer program product provides a user friendly platform for controlling the overall functionality of the inventive spectroscopic system. Hence, the computer program product provides selection of a particular probe head and serves to transmit appropriate control signals to the coupling unit in order to transmit excitation radiation to the selected probe head as well as to transmit respective return radiation to the spectroscopic analysis unit. Moreover, by means of the computer program product corresponding visual images that are collected by the selected probe head are displayed to the user of the spectroscopic system by means of the imaging unit.

It is to be noted, that the present invention is not restricted to a particular type of spectroscopic techniques, as e.g. Raman spectroscopy, but that other optical spectroscopic techniques can also be used. This includes (i) other methods based on Raman scattering including stimulated Raman spectroscopy and coherent anti-Stokes Raman spectroscopy (CARS), (ii) infra-red spectroscopy, in particular infra-red absorption spectroscopy, Fourier transform infra-red (FTIR) spectroscopy and near infra-red (NIR) diffusive reflection spectroscopy, (iii) other scattering spectroscopy techniques, in particular fluorescence spectroscopy, multi-photon fluorescence spectroscopy and reflectance spectroscopy, and (iv) other spectroscopic techniques such as photo-acoustic spectroscopy, polarimetry and pump-probe spectroscopy. Preferred spectroscopic techniques for application to the present invention are Raman spectroscopy and fluorescence spectroscopy.

Further, it is to be noted that any reference signs in the claims of the present application shall not be construed as limiting the scope of the invention.

In the following preferred embodiments of the invention will be described in detail by making reference to the drawings in which.

Figure 1:
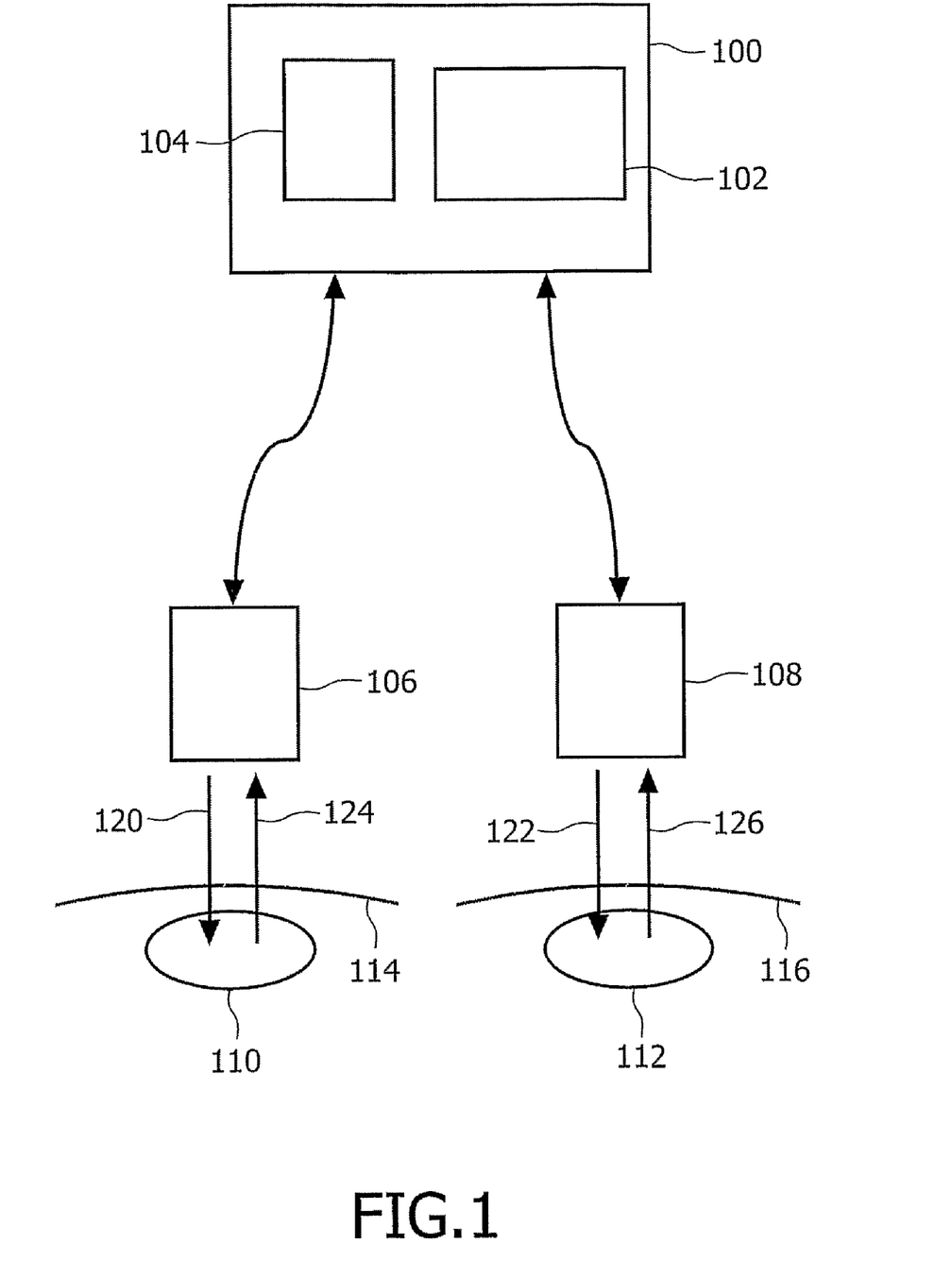
FIG. 1 shows a block diagram of the spectroscopic system having two probe heads.

FIG. 1 is illustrative of a block diagram of the inventive spectroscopic system. The spectroscopic system has a base station 100 that is connected to a first probe head 106 and to a second probe head 108. The base station 100 itself has a light source 104 and a spectroscopic analysis unit 102. The first and second probe heads 106, 108 are adapted to direct first and second excitation radiation 120, 122 into first and second volumes of interest 110, 112. The first probe head 106 focuses first excitation radiation 120 into the first volume of interest 110 and collects respective return radiation 124 emanating from the volume of interest 110.

Similarly, the second probe head 108 focuses second excitation radiation 122 into the second volume of interest 112. Also, the second probe head 108 is adapted to collect second respective return radiation 126 emanating from the second volume of interest 112. Generally, the inventive spectroscopic system can be universally applied to various volumes of interest 110, 112. Preferably, the inventive spectroscopic system is used to spectrally analyze a substance or various substances that are located inside or that form a particular or various particular biological structures that are located in the first and second volumes of interest 110, 112 respectively.

Preferably, the inventive spectroscopic system and the at least first and second probe heads 106, 108, are applied to various parts of the body of a single person or to various parts of various persons. In this case the first and the second volumes of interest 110, 112 are located underneath the surface of a skin 114, 116 of a particular person or of various different persons. In particular the inventive spectroscopic system is ideally suited for non invasive analysis of blood of a person that is flowing through e.g. blood vessels that are located within the volume of interest 110 or 112. This allows for an effective and non invasive analysis of the composition of blood of a person. For example, concentrations of glucose, blood oxygen and various other blood parameters can be effectively determined.

Typically, the first and the second probe heads 106, 108 are connected to the base station by mean of flexible fiber optical transmission media. These fiber transmission media serve to transmit first and second excitation radiation to the first and second probe heads 106, 108 respectively and to transmit collected return radiation 124, 126 to the spectroscopic analysis unit 102 of the base station 100. The light source 104 of the base station 100 is typically implemented as a NIR laser light source. The spectroscopic analysis unit 102 is preferably implemented as a commercially available spectrometer. It may be based on a combination of a grating and a cooled high precision CCD camera.

Since the laser light source 104 and the spectroscopic analysis unit 102 have to meet stringent requirements in order to guarantee a precise and reliable spectral analysis of the various volumes of interest 110, 112, appropriate light sources 104 and spectroscopic analysis units 102 are rather expensive.

Making use of a plurality of probe heads 106, 108 therefore allows to effectively exploit the entire capacity of the costly components of the base station 100. Moreover, the invention provides examination of various parts of a body of a person that might be useful in order to rule out position dependent effects in the blood compound determination. The choice of the site of a human body where a non invasive blood analysis measurement is conducted could have major impact on the measurement and hence the determination of the blood composition it might be necessary to monitor simultaneously multiple sites of a human body in order to diminish these possible effects. By making use of a plurality of probe heads 106, 108 therefore has the same effect as making use of a plurality of complete spectroscopic systems each having a separate light source and a separate spectroscopic analysis unit.

Figure 2:
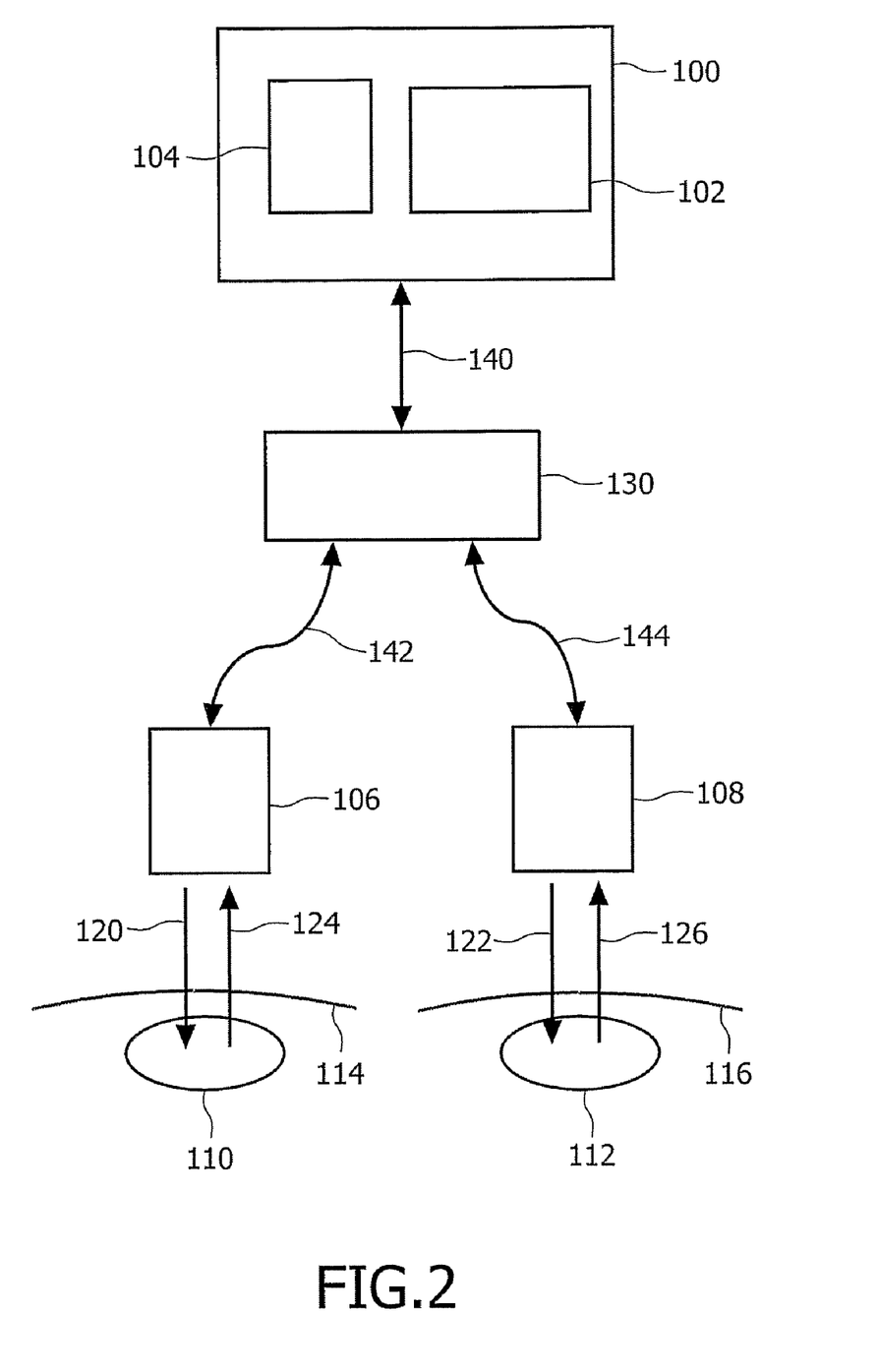
FIG. 2 shows a block diagram of the spectroscopic system with a coupling unit.

FIG. 2 illustrates a block diagram of the spectroscopic system that further implements a coupling unit 130 that provides coupling of excitation and return radiation between the base station 100 and the first and second probe heads 106, 108. The coupling unit 130 is connected to the base station 100 via an optical fiber 140 and is separately connected to the first probe head 106 via optical fiber 142. It is further connected to the second probe head 108 via optical fiber 144.

All illustrated optical fibers 140, 142, 144 are adapted to provide bi-directional transmission of optical signals, i.e. excitation and return radiation. In the illustrated embodiment, the coupling unit allows selection of one particular probe head for spectroscopic analysis of a substance in a corresponding volume of interest. For example, by selecting the first probe head 106 the optical fibers 140 and 142 provide transmission of excitation radiation 120 and return radiation 122 between the probe head 106 and the base station 100. While the first probe head 106 is selected only return radiation 124 collected by the probe head 106 can be effectively transmitted to the spectroscopic analysis unit 102 because the optical fiber 140 only allows transmission of a single broadband optical signal. Therefore, while probe head 106 is selected second return radiation 126 collected by probe head 108 cannot be transmitted to the spectroscopic analysis unit 102 via the optical fiber 140.

In the illustrated embodiment the coupling unit 130 acts as a switch for selecting a particular return radiation that can be spectrally analyzed by the spectroscopic analysis unit 102.

Generally, the light source 104 does not have to be implemented into the base station 100. Alternatively, it may be realized as a separate unit and can in principle also be incorporated into the probe head 106, 108 when applicable. This allows for an even larger flexibility of spectroscopic system.

Figure 3:
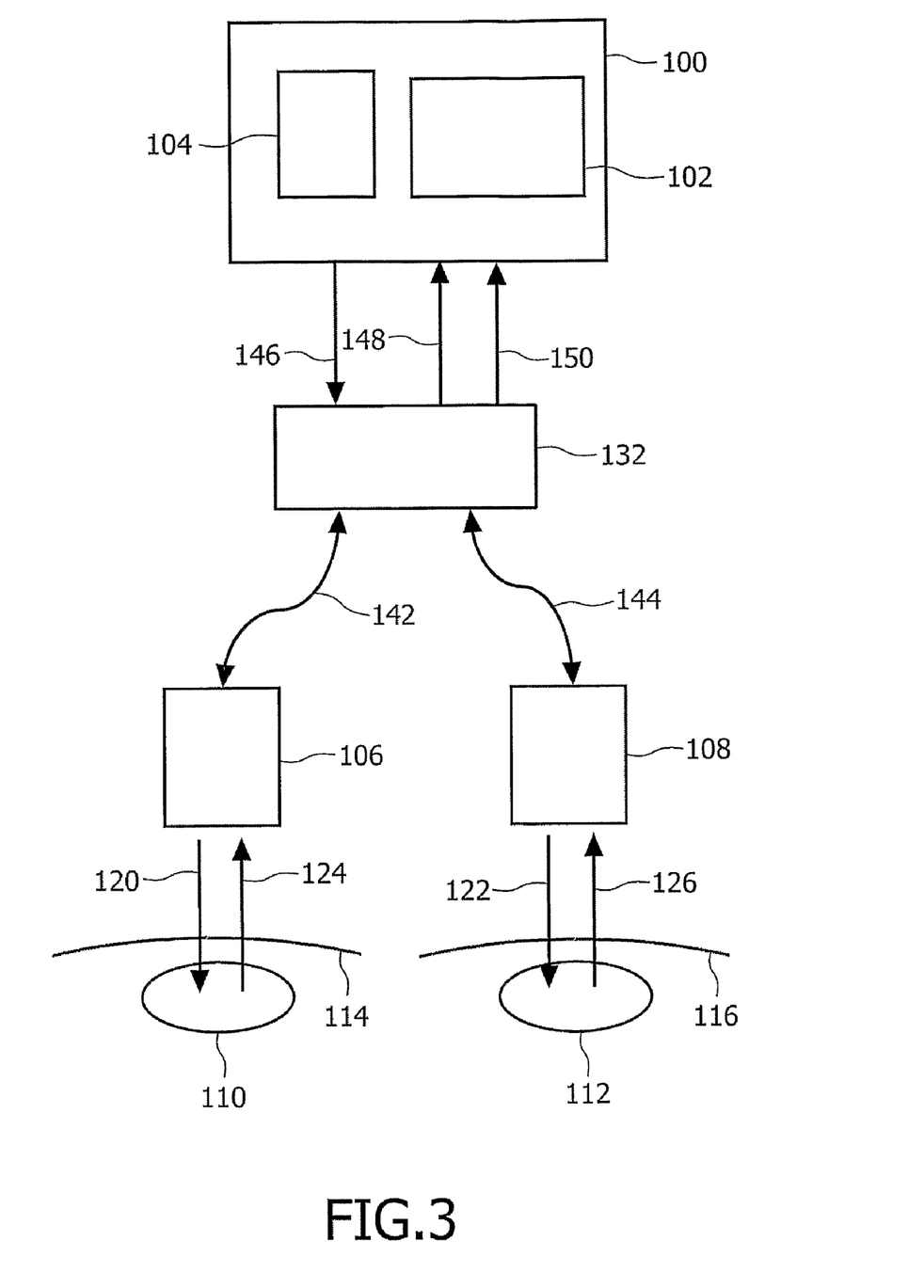
FIG. 3 shows an alternative block diagram of the spectroscopic system with the coupling unit.

FIG. 3 shows a block diagram of a preferred implementation of the coupling unit 132. Similar as already depicted in FIG. 2 the coupling unit 132 is connected to the first probe head 106 via the optical fiber 142 and is further connected to the second probe head 108 via the optical fiber 144. In contrast to the embodiment depicted in FIG. 2 the coupling unit 132 is connected to the base station 100 via a plurality of optical fibers 146, 148 and 150. Optical fiber 146 provides excitation radiation generated by the light source 104 to the coupling unit 132. The coupling unit 132 then couples the received excitation radiation either into optical fiber 142 or optical fiber 144. Alternatively, the coupling unit 132 may also split the received excitation radiation into a first and second excitation radiation that are simultaneously coupled into optical fibers 142, 144, respectively.

In this way excitation radiation generated by the light source 104 and transmitted to the coupling unit 132 can be split into a plurality of separate excitation radiations or excitation beams that are separately coupled to respective probe heads. In this way various volumes of interest 110, 112 can be spectrally analyzed simultaneously.

Since first and second return radiation 124, 126 have to be spectrally analyzed separately, the coupling unit 132 serves to couple first return radiation 124 received via optical fiber 142 into optical fiber 148. Similarly, second return radiation 126 might be coupled into optical fiber 150. Hence the spectroscopic signals that are received by the spectroscopic analysis unit 102 via the optical fibers 148, 150 are indicative of a molecular composition of substances that are located in the first and second volumes of interest 110, 112, respectively. In this way different substances in various volumes of interest 110, 112 can be simultaneously spectrally analyzed by the spectroscopic analysis unit 102 of the base station 100.

Alternatively, the coupling unit 132 may be implemented as a splitter with a restricted functionality in order to split excitation radiation received via optical fiber 146 and to couple the splitted components into optical fibers 142, 144 which may serve only to transmit excitation radiation. In this case optical fibers 148 and 150 that are adapted to transmit return radiation may also be directly connected to the probe heads 106, 108. In such an embodiment optical fibers 142, 144 only have to transmit excitation radiation to the various probe heads 106, 108 at the expense that each probe head 106, 108 has to be directly and separately connected to the base station 100 via optical fibers 148 and 150.

Figure 4:
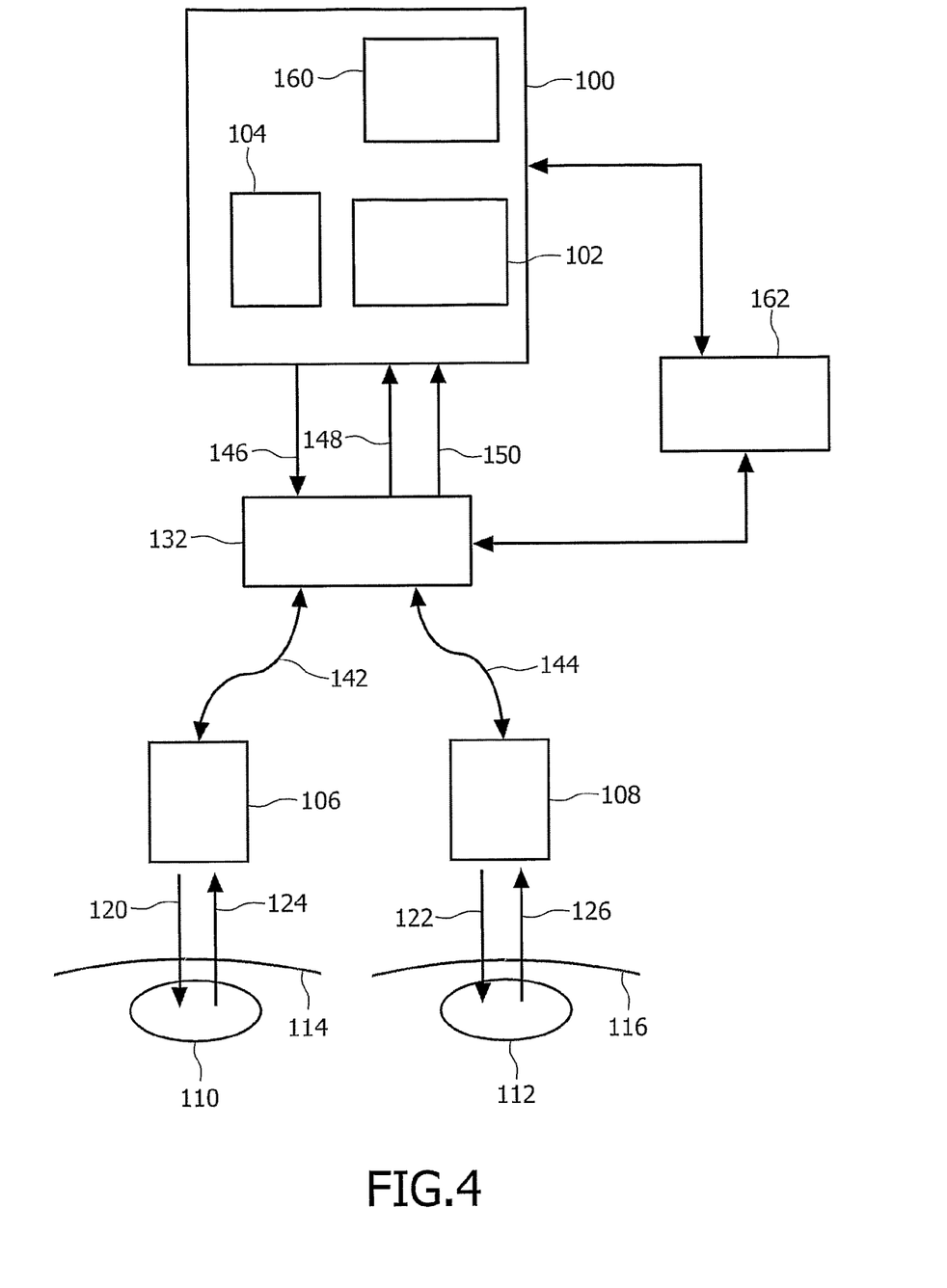
FIG. 4 shows a block diagram of the spectroscopic system making use of an imaging unit.

FIG. 4 shows a block diagram of an embodiment of the present invention incorporating an imaging unit 162 and a control module 160. In this particular embodiment the imaging unit 162 is implemented as a separate device that is connected to the coupling unit 132 and to the base station 100. The control module 160 is implemented as a module of the base station 100. The imaging unit 162 serves to provide visual images of a first and a second area of interest.

The first and the second area of interest describe a cross section that is substantially larger than a volume of interest. Visualizing an area of interest allows to identify biological structures or particular substances that shall become subject to spectroscopic analysis. Identified biological structures can then be effectively defined as a volume of interest. Required overlapping of the volume of interest, i.e. a dedicated biological structure and the spectroscopic inspection volume of the spectroscopic system, can be effectively realized by some kind of appropriate displacement and alignment means.

Typically, imaging of an area of interest is based on an imaging system making use of a separate light source that operates in a different wavelength region than the spectroscopic light source 104 of the base station 100. However, the probe heads 106, 108 are adapted to support both spectroscopic analysis as well as visual imaging of an area of interest and a volume of interest, respectively.

The control module 160 is adapted to control an interplay between light source 104, spectroscopic analysis unit 102, coupling unit 132 and imaging unit 162. By means of the control module 160 a particular probe head 106 can be effectively selected by a user of the spectroscopic system. In response to a user defined selection of a probe head 106, the control module 160 controls the coupling unit 132 to direct excitation radiation into the probe head 106 and to conduct respective return radiation 124 to the spectroscopic analysis unit 102. Additionally, the control module 160 submits corresponding control signals to the imaging unit 162 that provides a visual image of an area of interest corresponding to the volume of interest 110. Hence, the control module 160 coordinates the functionality of the various components of the inventive spectroscopic system.

Alternatively, the imaging unit 162 can be implemented into the base station 100. In another alternative embodiment, each probe head 106, 108 can be provided with a separate imaging unit 162. This is particularly advantageous when the various probe heads 106, 108 are operated in spatially separated environments, like in different rooms of a hospital. Various operators or users of the plurality of probe heads 106, 108 may then make separate use of the different visual images of different areas of interest provided by a plurality of imaging units in order to appropriately allocate the different volumes of interest 110, 112 and to separately initiate or control application of spectroscopic analysis to the different volumes of interest 110, 112.

Figure 5:
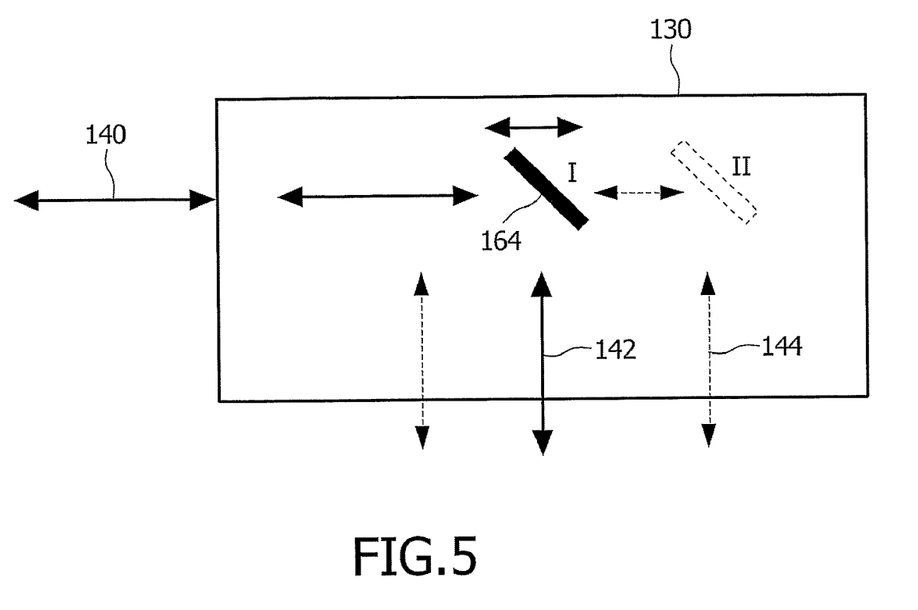
FIG. 5 illustrates a preferred embodiment of the coupling unit making use of a moveable mirror.

FIG. 5 illustrates an embodiment of the coupling unit 130 that can be incorporated into an inventive spectroscopic system as schematically shown in FIG. 2. The coupling unit 130 is adapted to be coupled to the base station via the optical fiber 140 and is further adapted to be coupled to the first and the second probe heads 106, 108 via the optical fibers 142, 144, respectively. All three fibers 140, 142, 144 are adapted to provide bidirectional transmission of excitation and return radiation between the probe heads 106, 108 and the base station 100. In this embodiment the coupling unit 130 serves as a kind of switch to select a single one of the plurality of probe heads 106, 108. Therefore, the coupling unit 130 can be realized with a limited number of functional components. In this case coupling of optical signals between optical fibers 140 and 142 or 140 and 144 can effectively be realized by a moveable mirror element 164. Preferably, the moveable mirror 164 is mounted on a translation stage that provides a horizontal movement of the mirror 164 as indicated by the arrow. When the mirror 164 is in position I optical signals are effectively coupled between the optical fibers 140 and 142. This effectively leads to an activation and selection of the first probe head 106 that is connected to the optical fiber 142.

Moving of the moveable mirror 164 to position II effectively allows to couple excitation radiation received via optical fiber 140 into optical fiber 144. In this way the probe head 108 that is connected to optical fiber 144 is effectively selected. Consequently, return radiation 126 collected by probe head 108 is effectively coupled to the optical fiber 140 resulting to transmission of return radiation 126 to the spectroscopic analysis unit 102 of the base station 100.

In this embodiment the coupling unit is adapted to either select the first or the second probe head 106, 108 for spectroscopic analysis of a corresponding volume of interest 110, 112.

Figure 6:
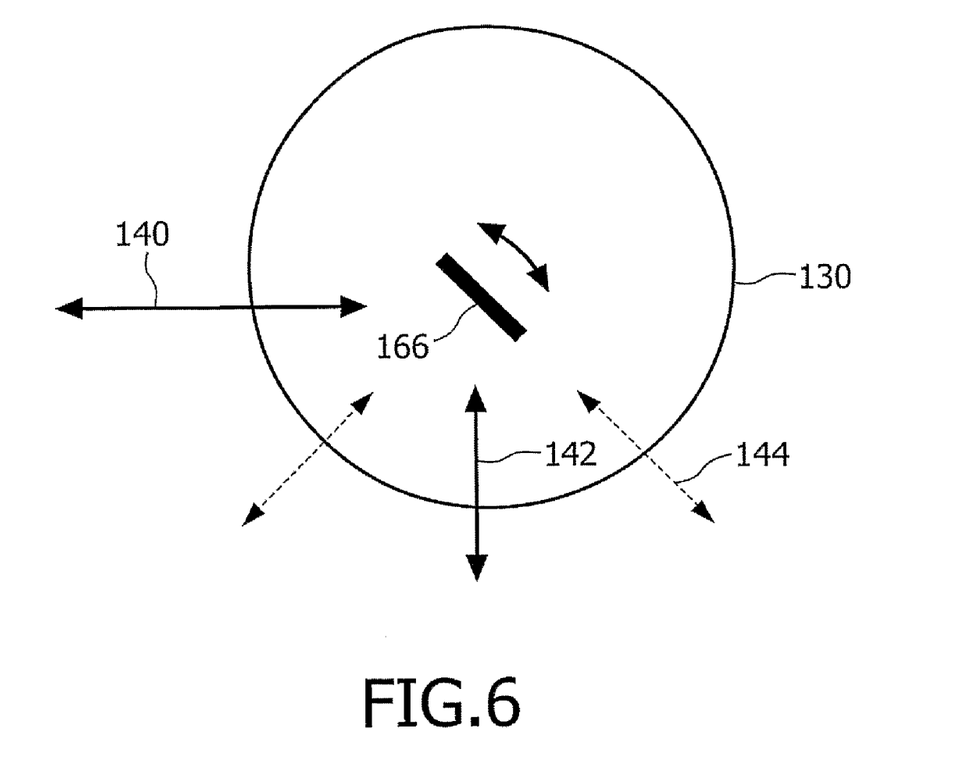
FIG. 6 illustrates another preferred embodiment of the coupling unit making use of a rotatable mirror.

FIG. 6 shows an alternative embodiment of the coupling unit 130 making use of a rotatable mirror 166 instead of a moveable mirror 164. Here, by appropriately rotating the mirror 166 optical signals can be coupled between optical fiber 140 and optical fiber 142 or between optical fiber 140 and optical fiber 144.

Figure 7:
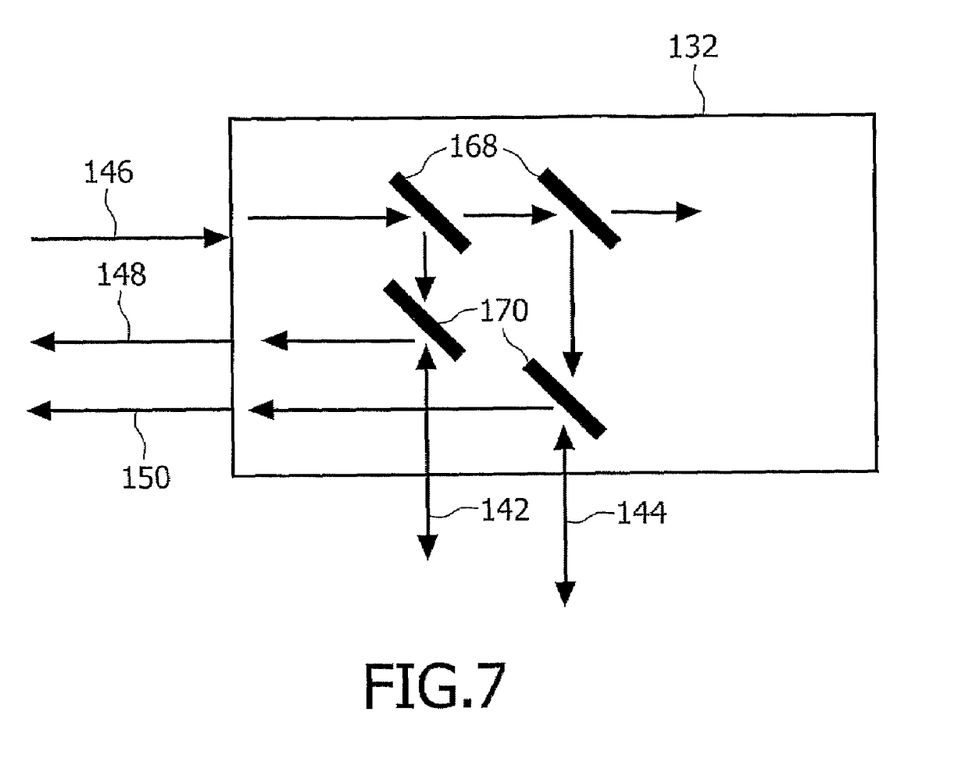
FIG. 7 illustrates another preferred embodiment of the coupling unit for splitting excitation radiation.

FIG. 7 illustrates a typical embodiment of a coupling unit 132 that can be implemented into an embodiment of the spectroscopic system as illustrated in FIG. 3 and FIG. 4. The coupling unit 132 is connected to the base station 100 via optical fibers 146, 148, 150 and is further connected to the first probe head 106 via optical fiber 142 and to the second probe head 108 via optical fiber 144. The coupling unit 132 has a plurality of beam splitters 168 and dichroic mirrors 170. Excitation radiation that is received from the light source 104 of the base station 100 via the optical fiber 146 is split into at least two optical beams by means of the beam splitters 168. Depending on the transmission and/or reflection properties of the beam splitters 168, the intensity of the first and the second excitation radiation that are coupled into the optical fibers 142, 144 can be arbitrarily modified. First and second return radiation that enter the coupling unit 132 via the optical fibers 142, 144 is reflected by the dichroic mirrors 170 and therefore separately coupled into the optical fibers 148 and 150. In this way first and second return radiation 124, 126 are separately coupled into optical fibers 148, 150 allowing for a separate and simultaneous spectroscopic analysis by means of the spectroscopic analysis unit 102.

The dichroic mirrors 170 are specially designed for the wavelength of the excitation radiation and the frequency shifted return radiation. Preferably the dichroic mirrors 170 feature a high transmission for the excitation radiation and high reflectivity for return radiation that is frequency shifted with respect to the excitation radiation.

In an alternative embodiment where each probe head is separately connected with the base station for transmission of return radiation that each of the probe heads has to incorporate a separate dichroic mirror element for appropriately spatially separating excitation and return radiation.

Figure 8:
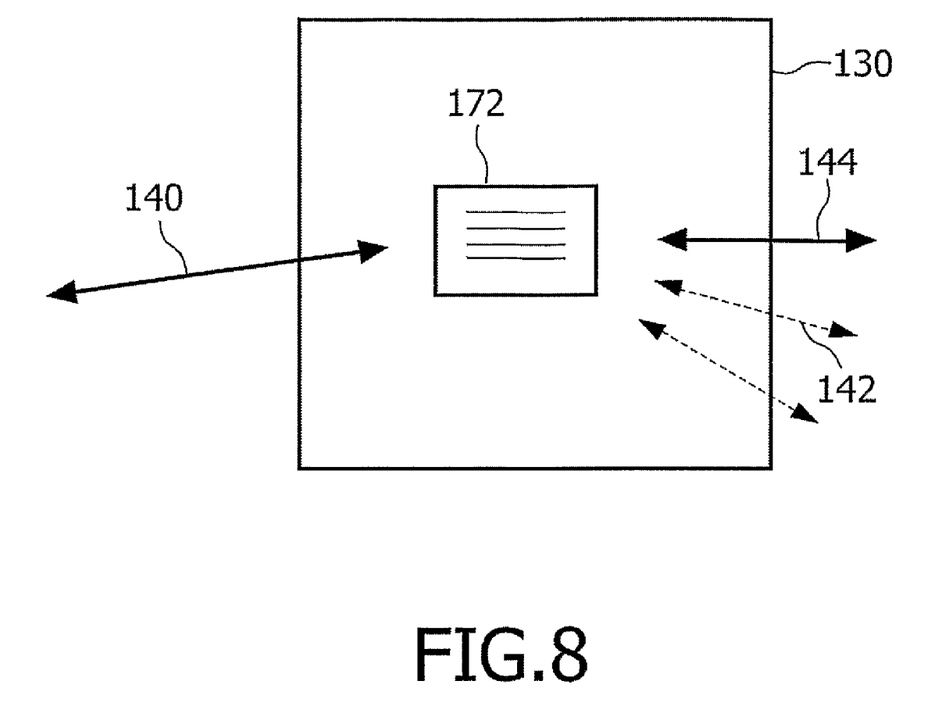
FIG. 8 illustrates a block diagram of the coupling unit making use of an electrooptic modulator.

FIG. 8 is illustrative of another alternative embodiment of the coupling unit 130 making use of an electrooptic or acoustooptic modulator 172. The illustrated embodiment of the coupling unit 130 provides the same functionality than the embodiments of the coupling unit illustrated in FIG. 5 and FIG. 6. Excitation radiation that is received from the light source 104 of the base station 100 via optical fiber 140 is directed on the electrooptic modulator 172 where it becomes subject to diffraction and/or spatial deflection. For example, the electrooptic modulator is adapted to generate tunable gratings leading to sufficient redirection of the excitation radiation into any one of the optical fibers 144, 142. In a similar way return radiation received via optical fibers 142, 144 can be coupled into the fiber 140 providing transmission of return radiation to the spectroscopic analysis unit.

The illustration of the various embodiment of the coupling unit in FIGS. 5 to 8 are only schematic in order to show the coupling mechanism of the various coupling units. They may further comprise additional light shaping optical elements such as lenses for appropriately focusing and coupling the optical beams into the various optical fibers.

Figure 9:
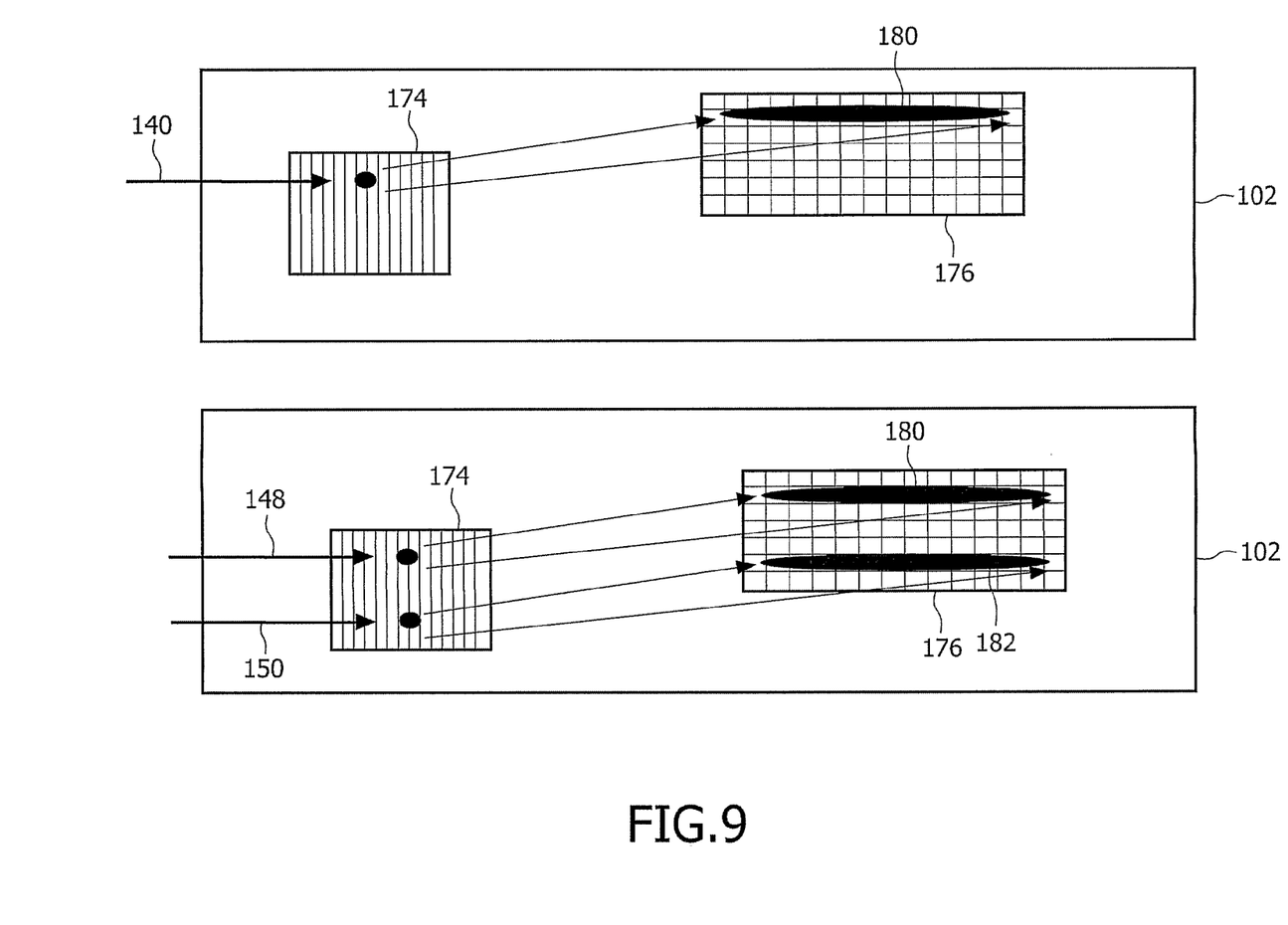
FIG. 9 is illustrative of a simultaneous detection of multiple spectroscopic signals.

FIG. 9 schematically illustrates the functionality of the spectroscopic analysis unit 102. In the upper illustration return radiation transmitted via optical fiber 140 is directed onto a grating 174. By means of the grating 174 the various spectral components of the return radiation are spatially separated and imaged onto a CCD chip 176. The various spectral components of the return radiation are then spatially separated as a spectrum 180.

The bottom illustration of FIG. 9 shows an alternative embodiment of the spectroscopic analysis unit 102 that is adapted for simultaneous detection and spectral analysis of a plurality of spectroscopic signals. In this case two spectroscopic signals that are provided by the separate optical fibers 148 and 150 are both directed onto the grating at different vertical positions. The resulting spectra 180, 182 are then projected at different vertical positions of the CCD chip 176. In this way two different spectra 180, 182 can be effectively analyzed in a simultaneous way. The number of spectra that can be simultaneously analyzed is limited by the vertical size of the spectra 180, 182 and the vertical size of the CCD chip 176.

Preferably, the bottom illustration of FIG. 9 can be ideally coupled to a coupling unit that provides two separate optical fibers 148, 150 for transmission of first and second return radiation. Such a coupling unit is for example depicted in FIG. 7. The coupling unit of FIG. 7 provides efficient coupling of first and second return radiation into the optical fibers 148, 150 for transmission of first and second return radiation to the spectroscopic analysis unit 102. In this way, return radiation acquired from different and spatially separated volumes of interest 110, 112 can be spectrally analyzed in a simultaneous way by combining the embodiment shown in FIG. 7 and in the bottom illustration of FIG. 9.

The present invention provides a spectroscopic system with multiple probes that effectively allows to share the costly and high precision components of a spectroscopic analysis system. Applying multiple probes to a base station providing a laser light source and a high precision spectroscopic analysis unit effectively allows to simultaneously spectrally analyze various biological structures that are located at different parts of a body of a person or even in different parts of various persons that are spatially separated. The present invention is therefore ideally suitable to hospitals for effectively sharing spectroscopic analysis capacity. In particular making use of dedicated coupling units allows for a flexible and reconfigurable implementation of the spectroscopic system.

LIST OF REFERENCE NUMERALS 100 base station
102 spectroscopic analysis unit
104 light source
106 probe head
108 probe head
110 volume of interest
112 volume of interest
114 skin
116 skin
120 excitation radiation
122 excitation radiation
124 return radiation
126 return radiation
130 coupling unit
132 coupling unit
140 optical fiber
142 optical fiber
144 optical fiber
146 optical fiber
148 optical fiber
150 optical fiber
160 control module
162 imaging unit
164 movable mirror
166 rotatable mirror
168 beam splitter
170 dichroic mirror
172 optical modulator
174 grating
176 CCD chip
180 spectrum
182 spectrum

The invention claimed is:

1. A spectroscopic system for determining of a property of a substance at a plurality of volumes of interest comprising:
   a base station having a multi-channel spectroscopic analysis unit and a light source for providing excitation radiation;
   a plurality of a probe heads directing the excitation radiation into the plurality of volumes of interest and collecting return radiation emanating from the plurality of volumes of interest;
   a plurality of bidirectional optical coupling fibers, each optical coupling fiber carrying excitation radiation to a corresponding probe head and return radiation from the corresponding probe head;
   an optical router (a) selectively channeling the excitation radiation to the optical coupling fiber corresponding to each of the probe heads and (b) selectively switching the return radiation from the optical coupling fiber corresponding to each of the probe heads to a selected channel of the multi-channel spectroscopic analysis unit.

2. The spectroscopic system according to claim 1, wherein there is a larger plurality of probe heads than channels in the analyzer unit.

3. A spectroscopic system for determining of a property of a substance at a plurality of volumes of interest comprising:
   a base station having a multi-channel spectroscopic analysis unit and a light source for providing excitation radiation;
   a plurality of a probe heads directing the excitation radiation into the plurality of volumes of interest and collecting a return radiation emanating from the plurality of volumes of interest; and an optical router (a) selectively channels the excitation radiation to each of the probe heads and (b) selectively switching return radiation from each of the plurality of probe heads among the channels of the spectroscopic analysis unit, the spectroscopic analysis unit spectrally analyzing return radiation from some of the probe heads concurrently and some of the probe heads sequentially.

4. A computer program product for a spectroscopic system for determining of a property of a substance in at least first and a second volumes of interest, the spectroscopic system having an excitation light source, a return light analysis unit, and a coupling unit which selectively supplies the excitation radiation to a plurality of probe heads and switches return radiation from each of the probe heads to the analysis unit to be spectroscopically analyzed, the computer program product comprising:

program means for intermittently selecting each of the probe heads to receive the excitation radiation, program means for directing the excitation radiation to each selected probe head, program means for intermittently switching the return radiation collected by each of the probe heads to the analysis unit for individual spectroscopic analysis, and program means for controlling the spectroscopic analysis to analyze return radiation from some of the robe heads concurrently and some of the robe heads sequentially.

5. The computer program product of claim 4, further including:

a program means for mapping each spectroscopic analysis to a corresponding one of the probe heads.

6. A spectroscopic system for determining of a property of a substance in at least first and second volumes of interest, the spectroscopic system comprising:

a base station having a light source and a spectroscopic analysis unit;

at least a first and a second probe head;

a coupling unit providing a coupling between the base station and any of the at least first and second probe heads and selectively coupling the first and a second probe head to the base station for directing at least a first and a second excitation radiation into the at least first and second volumes of interest and for collecting at least a respective first and second return radiation;

a first bidirectional optical fiber for selectively directing excitation radiation from the coupling unit to the first probe head and the return radiation from the first probe head back to the coupling unit; and a second bidirectional optical fiber for selectively directing the excitation radiation from the coupling unit to the second probe head and the second probe head back to the coupling unit.

7. The spectroscopic system according to claim 6, further comprising:

an imaging unit that provides at least a first image of a first area of interest and a second image of a second area of interest.

8. The spectroscopic system according to claim 6, wherein the coupling unit selectively splits a radiation generated by the light source into the at least first and second excitation radiation, wherein the coupling unit selectively couples the at least first and second excitation radiation to the at least first and second probe heads.

9. The spectroscopic system according to claim 6, wherein the coupling unit:

couples the radiation from the light source to each of the bidirectional optic fibers to transmit the radiation from the light source to a selected one or more of the probe heads; and selectively couples the return radiation carried by each of the bidirectional optic fibers collected by each of the probe heads into one of a plurality of transmission media to connect the return radiation from each probe head to a channel of the spectroscopic analysis unit of the base station.

10. The spectroscopic system according to claim 6, further comprising:

a control module that controls the coupling of the at least first and second excitation radiation to the at least first and second probe heads and to control the coupling of the at least first and second return radiation to the base station.

11. The spectroscopic system of claim 6, wherein the spectroscopic analysis unit spectrally analyzes the at least first and second return radiation simultaneously.

12. The spectroscopic system according to claim 6, wherein the coupling unit includes an optical means which selectively directs excitation radiation based on mechanical movement of at least a portion of the optical means.

13. The spectroscopic system according to claim 6, wherein the coupling unit includes one of an electro-optic and an acousto-optic modulator which directs the excitation radiation to one or more of the bidirectional optic fibers.

14. The spectroscopic system according to 6, wherein the base unit and the coupling are located in an analysis area of a medical facility having a plurality of patient rooms including a first patient room and a second patient room, the first bidirectional optic fiber extending from the coupling unit in the analysis area to the first patient room and the second bidirectional optical fiber extending from the coupling unit in the analysis area to the second patient room, the first probe head being selectively coupled to the first bidirectional optic fiber in the first patient room for performing a spectroscopic examination of a first patient in the first patient room, the second probe head being selectively coupled to the second bidirectional optic fiber in the second patient room for concurrently performing a spectroscopic examination of a second patient in the second patient room.

15. The spectroscopic system according to claim 14, further including:

a control unit which controls the coupling unit for controlling coupling the base unit to each of the probe heads to concurrently spectroscopically examine a plurality of patients and maps the spectroscopic examination results with the corresponding patient.

* * * * *